(12) United States Patent
Lloyd et al.

(10) Patent No.: US 8,190,451 B2
(45) Date of Patent: May 29, 2012

(54) METHOD AND COMPUTER PROGRAM PRODUCT FOR PREDICTING AND MINIMIZING FUTURE BEHAVIORAL HEALTH-RELATED HOSPITAL ADMISSIONS

(75) Inventors: Karen D. Lloyd, Jordan, MN (US); Tammie J. Lindquist, Plymouth, MN (US); Lynne A. Dancha, Minneapolis, MN (US); Michael Koopmeiners, Maplewood, MN (US); Agnes W. H. Tan, Plymouth, MN (US)

(73) Assignee: Group Health Plan, Inc., Minneapolis, MN (US)

( * ) Notice: Subject to any disclaimer, the term of this patent is extended or adjusted under 35 U.S.C. 154(b) by 1192 days.

(21) Appl. No.: 11/299,511

(22) Filed: Dec. 12, 2005

(65) Prior Publication Data
US 2006/0224416 A1 Oct. 5, 2006

Related U.S. Application Data

(60) Provisional application No. 60/665,962, filed on Mar. 29, 2005.

(51) Int. Cl.
*Q06Q 10/00* (2006.01)
(52) U.S. Cl. .................................. 705/3; 705/1
(58) Field of Classification Search ............... 705/3
See application file for complete search history.

(56) References Cited

U.S. PATENT DOCUMENTS

| | | | |
|---|---|---|---|
| 6,059,724 A * | 5/2000 | Campell et al. ............ 600/300 |
| 2003/0050794 A1* | 3/2003 | Keck .............................. 705/2 |
| 2003/0195772 A1 | 10/2003 | Meek et al. |
| 2004/0015337 A1* | 1/2004 | Thomas et al. ............. 703/11 |

OTHER PUBLICATIONS

Johns Hopkins' ACG Risk Adjustment System Utilizes Predictive Modeling, Jan. 12, 2006 (3 pages).

* cited by examiner

*Primary Examiner* — Hiep V Nguyen
(74) *Attorney, Agent, or Firm* — Winthrop & Weinstine, P.A.

(57) ABSTRACT

An accurate predictive model that identifies the patient/members within the healthcare system at high risk of hospital admission for a wide range of morbidities, or co-morbidities, and that allows subsequent intervention to manage those patients identified as high risk to an acceptable level. There is a further need for such a predictive model that focuses on specific groupings of conditions, e.g., behavioral health predictive modeling. There is also a need for a method that provides for intervention to manage the risk to the identified patients/members. One embodiment of the present invention discloses and claims a method of high-risk patient identification and management. In one aspect, the inventive method may comprise compiling a listing including all individuals with any primary behavioral health diagnosis over a specified time period; merging the listing with at least one data source to extract at least one behavioral health-related predictive factor; generating, based on at least one predictive model, a predictive output comprising the probability that the individuals listed will require a future behavioral health-related hospital admission; identifying the high-risk individuals from the predictive model output; and intervening with the high risk members to identify and modify, to the extent possible, the risk factors that place the member at high risk.

19 Claims, 2 Drawing Sheets

METHOD AND COMPUTER PROGRAM PRODUCT FOR PREDICTING AND MINIMIZING FUTURE BEHAVIORAL HEALTH-RELATED HOSPITAL ADMISSIONS

CROSS-REFERENCE TO RELATED APPLICATIONS

The present application claims the benefit and priority of provisional application No. 60/665,962 filed Mar. 29, 2005, which is incorporated herein by reference thereto in its entirety, as though fully set forth herein.

INVENTORS

Karen D. Lloyd, PhD., L.P., a citizen of the United States residing at 18150 East Sioux Vista, Jordan, Minn. 55352;

Tammie J. Lindquist, a citizen of the United States residing at 10930 47$^{th}$ Place, Plymouth, Minn. 55442-2595;

Lynne A. Dancha, a citizen of the United States residing at 4101 17$^{th}$ Avenue South, Minneapolis, Minn. 55407;

Michael Koopmeiners, MD, a citizen of the United States residing at 2514 Montana Avenue, Apt. 117, Maplewood, Minn. 55119; and Agnes Tan, a citizen of the United States residing at c/o Therese Pui, 12855 34$^{th}$ Avenue North, Plymouth, Minn. 55441.

BACKGROUND OF THE INVENTION

1. Field of the Invention

The present invention is directed to a method and computer program product for identifying patients/members with a high risk of future behavioral health-related hospital admission and subsequently managing those individuals identified as a high risk to reduce the probability of hospital admission.

2. Description of the Related Art

One of many major challenges facing risk-bearing payer organizations in today's managed healthcare environment is to find a way to accurately prospectively identify its members that are considered high risk for utilization of the healthcare system. A second challenge is intervening after identification to maximize the health of the high-risk members. With the appropriate predictive methodology, the payer organization may identify those members considered high risk, e.g., to be at risk of hospital admission and then proactively intervene to assist the identified members modify the risk factors that place them at high risk.

The need for such a method is especially acute in the context of behavioral health issues. Approximately 5% of patients with a recorded diagnosis of a behavioral health condition, e.g., depression or chemical dependency, are hospitalized for a behavioral health-related condition within twelve months of the initial diagnosis. These hospitalized patients incur approximately 50% of the overall total costs for behavioral health professional and facility services. Thus, it is very important that the 5% of patients most at risk of hospitalization due to a behavioral health-related condition are identified and the associated behavioral health condition managed through intervention where possible. Successful intervention will allow these patients to lead more healthy lives and save costs associated with hospitalization while freeing up behavioral health professional and facility resources.

Health plan and provider organizations currently use a variety of methods to screen or evaluate patients for inclusion in health management or case management programs. Some existing methods use claims data to target persons with high prior-cost levels, e.g., Diagnostic Cost Groups, or those with a certain medical condition, e.g., diabetes. Perhaps the most common risk adjustment mechanism in the insurance industry comprises age and gender adjustment. Still others apply survey-based assessment tools. One survey-based approach is described in US patent application publication number 2003/019522, to Meek, et al. Meek discloses a method of developing a risk level for the individual patient utilization of health care services by first obtaining subjective information from the individual patient about his or her perceived health. Meek then generates a risk level for that patient.

Meek's reliance upon subjective data obtained from patients concerning their individual perceived health requires improvement. Such subjective data is simply not as reliable as such data is when combined with additional data derived from a variety of data source(s).

Finally, Johns Hopkins has developed an "Adjusted Clinical Group" (ACG) based risk adjustment methodology. The Johns Hopkins method uses "Adjusted Clinical Groups" (ACGs), which are a series of mutually exclusive, health-status categories that are defined by morbidity, age and gender. They are based on the premise that the level of resources necessary for delivering appropriate health care to a population is correlated to the illness burden of that population. Thus, ACG's are employed in the Johns Hopkins method to predict a population's past or future health care utilization and costs. Essentially, the ACG method leverages the fact that over time, patient/members develop a variety of conditions. Based on the pattern of these conditions, the ACG method assigns each individual to a single group or ACG, thus permitting the effects of a clustering of conditions to be captured in estimates of resource use.

In practice, the Johns Hopkins method assigns all ICD-9-CM codes to one of 32 adjusted diagnosis groups ("ADG"). Diseases may then be placed in an ADG based on the following clinical parameters: Duration; Severity; Diagnostic Certainty; Etiology; and Specialty Care. Thus, all diseases must be classified using such clinical parameters and categorized into the 32 existing ADG's. Ultimately, an algorithm is applied that places patient/members into one of 93 discrete ACG categories. An individual patient/member will be assigned to an ACG based upon his/her particular combination of ADG's as well as his/her age and gender. The net result is that individuals with a certain ACG have experienced a similar morbidity pattern and consumed similar levels of health care resources over the course of a given period of time.

Several problems exist with the Johns Hopkins approach. One of the primary difficulties with ACG's involve a practice referred to commonly within the industry as "upcoding." Upcoding occurs when providers use diagnoses that result in their patients appearing to have more complicated illnesses than is really the case in order to benefit from additional resources or improve their ratings on case mix, i.e., ACG, adjusted measures of performance. Moreover, because ACGs are mutually exclusive, health status categories defined by morbidity, age and gender, patient/members must fit within a single ACG, thus comparatively less ill (or more ill) individual patients may not be well represented by the "average" illness burden across the entire ACG. Specifically, the Johns Hopkins ACG approach may mask the predictive effects of certain individual patient variables by categorizing patients first into ADG's, then into ACG's, two generalized diagnostic categorization tools for actuarial analysis. The Johns Hopkins ACG method is tuned to predict costs for actuarial purposes, it is not tuned to predict cases where interventions could reduce costs & improve quality.

In general, each existing approach to identification of patients for inclusion in a health management program is filled with problems, including inter alia, error and failure to utilize a predictive model to identify patients for prospective intervention, while still others are inadequate to apply across a wide range of patient morbidities, co-morbidities and other patient-specific variables. Finally, no approach deals specifically with behavioral health predictive methodology.

The invention described herein is a solution to many of the aforementioned problems with current approaches to high-risk patent identification.

BRIEF SUMMARY OF THE INVENTION

Given the situation described above there is a need for an accurate predictive model that identifies the patient/members within the healthcare system at high risk of hospital admission for a wide range of morbidities, or comorbidities, and that allows subsequent intervention to manage those patients identified as high risk to an acceptable level. There is a further need for such a predictive model that focuses on specific groupings of conditions, e.g., behavioral health predictive modeling. There is also a need for a method that provides for intervention to manage the risk to the identified patients/members.

One embodiment of the present invention discloses and claims a method of high-risk patient identification and management. In one aspect, the inventive method may comprise: developing a predictive mathematical model for at least one patient variable; compiling a member population dataset; running the population dataset against the predictive model; determining the probability of hospital admission for each population dataset member; identifying the target population, i.e., those members at high risk; and intervening with the high risk members to identify and modify, to the extent possible, the risk factors that place the member at high risk.

In another embodiment, the present invention discloses and claims a method of identifying patients at high risk for hospital admission due to behavioral health issues.

An object of the present invention is to provide a predictive high-risk behavioral health patient identification and management method, system and computer program product.

Another object of the present invention is to provide a predictive high-risk patient identification and management method, system and computer program product that identifies members at high risk of hospital admission based on a plurality of behavioral health related variables.

Another object of the present invention is to provide a predictive high-risk patient identification and management method, system and computer program product that facilitates proactive intervention for the members identified as high risk for behavioral health conditions.

The figures and the detailed description that follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
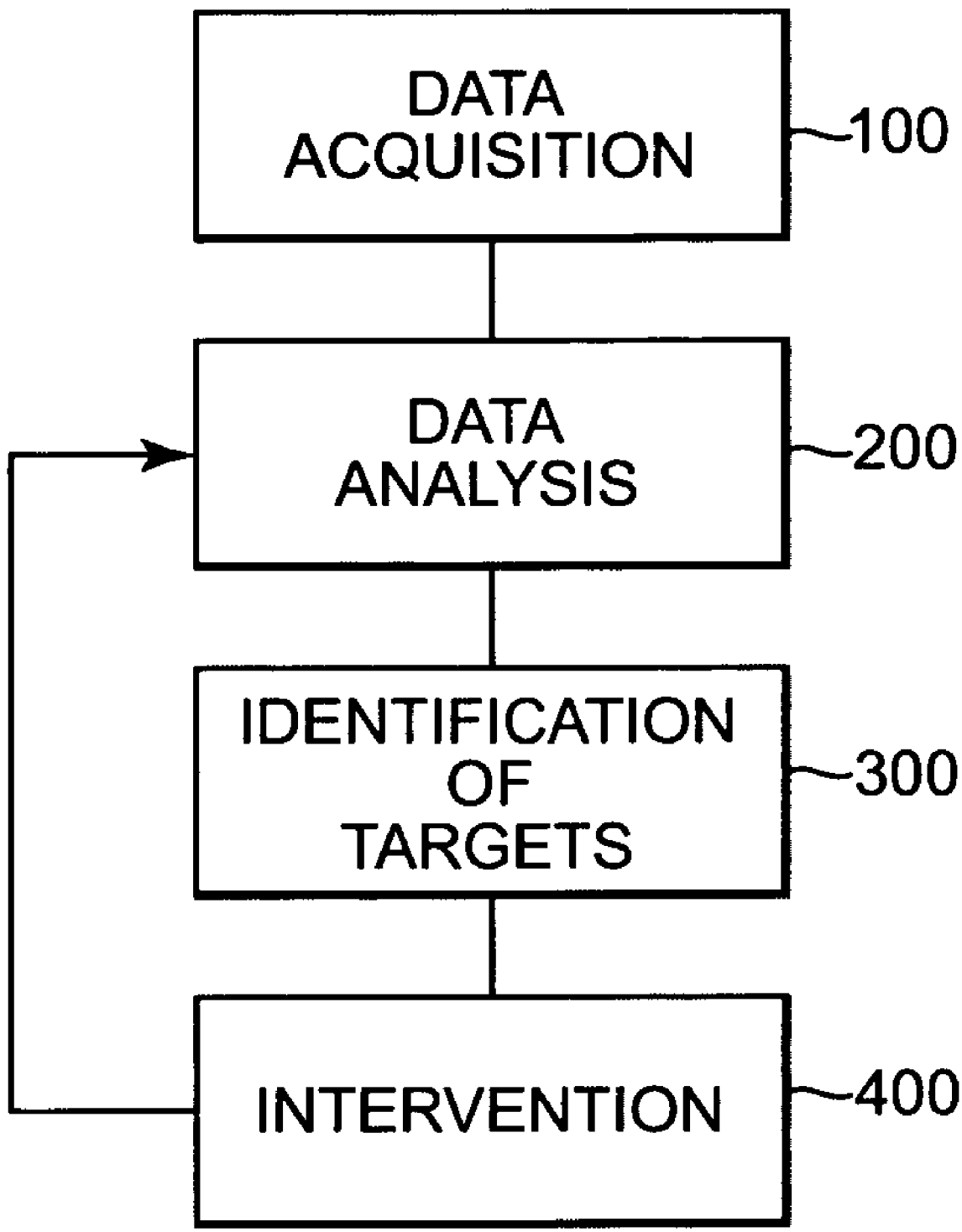
FIG. 1 is a simplified block diagram of an embodiment of the inventive method for predicting and minimizing future behavioral health-related hospital admissions.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

With reference to the Figures, a method, system and computer program product for identifying patients/members with a high risk of future hospital admission and subsequently managing those identified as a high risk to reduce the probability of hospital admission is described.

Specifically with reference to FIG. 1, one embodiment of the invention may comprise several modules. The first may be a data acquisition module 100. This module comprises generally the acquisition of patient and/or member data relating to any variable that may have a predictive influence on future hospitalization. Examples of the plurality of variables include, without limitation:

age;

gender;

primary or secondary diagnosis of specified diseases or morbidities or other conditions such as, inter alia, adjustment disorder, anxiety, bipolar, chemical dependency, depression, eating disorder, personality disorder, psychosis, schizophrenia, mental health issues generally, gastrointestinal problems, infectious diseases, rheumatology, cardiovascular disease, coronary artery disease, diabetes, pulmonary disease, thyroid disease, seizures, cancer, prescription drug use, evidence of non-prescriptive drug use/abuse, alcohol use and/or abuse;

number and timeframe of hospital admissions, including inter alia, admits for surgery, behavioral health issues, general health issues, mental health issues, chemical health issues, and admits through emergency room;

number of behavioral health office therapy visits and number of providers seen for same;

types of lab testing done; and whether the patient visited healthcare facility for preventive services.

It is understood that the above variable listing is exemplary only and comprises, in various embodiments, any variable that may have predictive value in determining whether an individual will require a hospital admission in the future for behavioral health-related conditions, diseases and the like.

The data acquisition involving the patient/member variables described above may be accomplished using many approaches, including inter alia, mining of billing records, claims history, pharmaceutical history, historical patient records, current patient records, patient self-reporting or any combination thereof.

The second module in various embodiments may comprise data analysis 200. In this module, the previously acquired data may be analyzed using at least one predictive mathematical model. The at least one predictive model is designed to determine the probability of a hospital admission for each patient/member. The predictive model(s) may be developed using historical patient or member data and may be further modified over time to more accurately predict the clinical outcome for individual patients. Those skilled in the art will readily recognize several possible mathematical and statistical approaches to solving this problem. For instance, ordinal, binomial or multinomial logistic regression may be employed. Ordinary least squares regression modeling may also be utilized and is within the scope of the present invention.

The third module may comprise identification of target patients/members 300. This module may further comprise determining from the probability output of the predictive model(s) which patients are considered "high risk" for future hospital admission. For certain diseases or conditions, or groups of diseases and/or conditions, this "high-risk" threshold may be those individuals falling within the top 5% of the predictive model results. For other conditions, the high-risk threshold may be the top 1 % of those individuals analyzed. The high-risk threshold is a function of the severity of the particular disease and/or condition and the impact of same on the health and well being of the individual patient/member as well as the cost of hospitalization based upon the disease(s) and/or condition(s) under consideration. In addition, the high-risk threshold may be modified over time in order to provide the model the most accurate predictive power.

Finally, the fourth module may comprise interventional risk management 400. In this module, the individuals previously identified as "high risk" are referred to caseworkers who may evaluate the individual's specific medical history and identify certain risk factors that aid in the categorization of the person as "high risk." The caseworker then may work with the individual and, in some cases, the individual's health care provider to reduce, eliminate or mitigate some or all of the risk factors to reduce the risk of the individual being admitted to a hospital in the future.

The inventive method may be improved through experience in several ways. First, the outcomes in intervention step 400 may inform the data analysis step 200. For example, the mathematical/statistical models used may be modified over time to better reflect interventional outcomes and improve the predictive power of the inventive method. Second, the data acquired over time in terms of the predictive factors comprising step 100 may change over time to improve predictive power. Moreover, the identification of targets in step 300 may change over time to provide more predictive results.

In general, the inventive method may be viewed in certain embodiments as a learning model wherein predictive power improves with time and experience. Modifications to the model and/or method may come from several sources and be used to improve the predictive results in several ways. For example, changes in member population over time may require changing aspects of the method. In addition, changes in professional healthcare provider practices over time may provide opportunities for changing aspects of the method with resulting enhancement of predictive results. Changes in data collection capabilities may occur and allow modification of the method and/or model. Finally, changes in methods to ameliorate the predictive or risk factors may occur.

The inventive method may be accomplished by performing the functions associated with above-described modules on a periodic basis. For example, the method may be performed daily, weekly, bi-weekly, monthly, quarterly, every six months, annually or other frequency. In addition, alternate embodiments may comprise the current time point probability data being statistically combined with probability data from previous time points to develop a moving average for evaluation purposes. This moving average data may be used, among other things, to evaluate the accuracy of the at least one predictive model and provide opportunity to improve the model(s).

Figure 2:
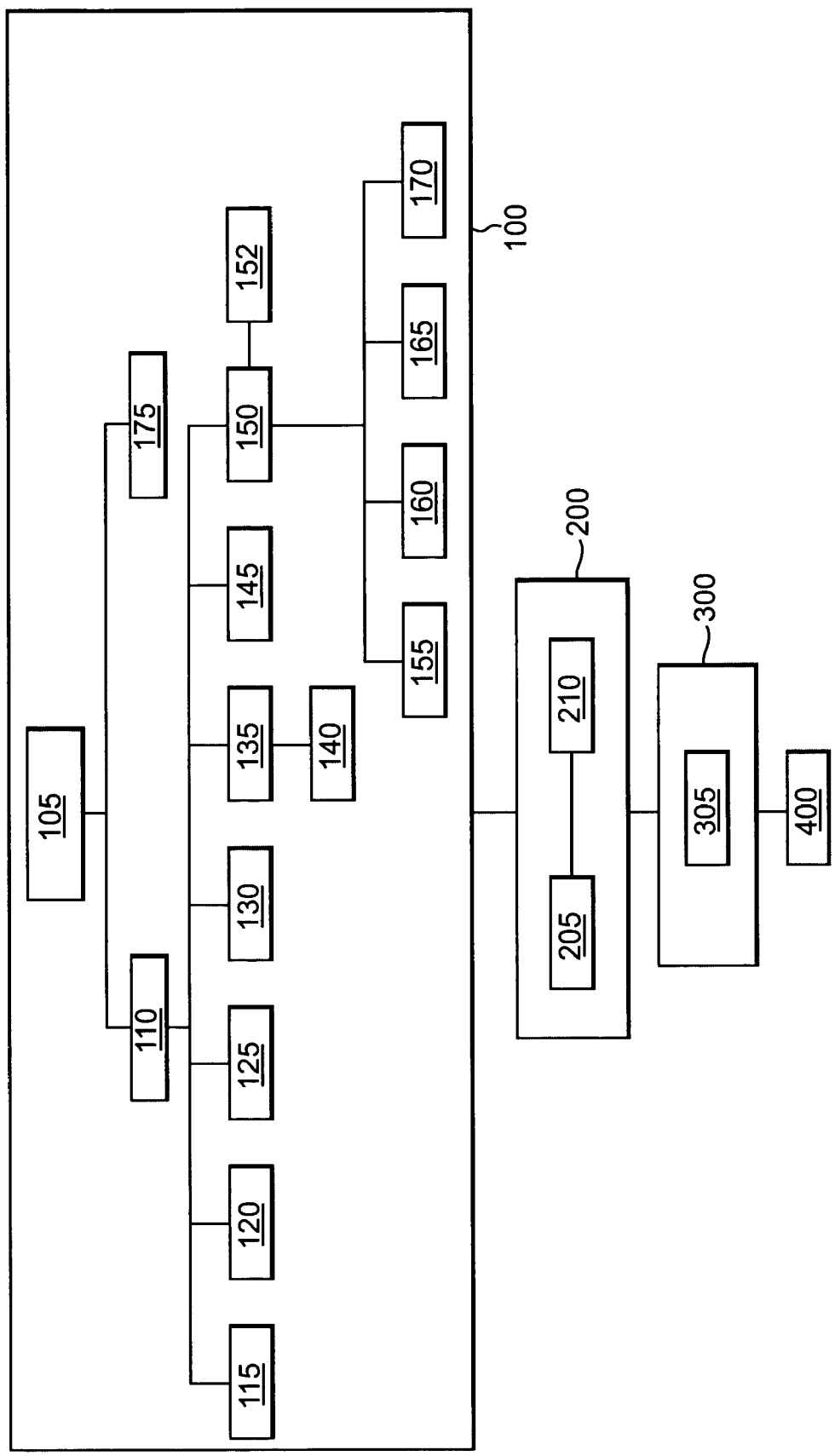
FIG. 2 is a program schematic illustrating an embodiment of the inventive method for predicting and minimizing future behavioral health-related hospital admissions.

Referring now to FIG. 2, a program level illustration of one embodiment of the inventive method is provided.

Initially, the data acquisition module 100 will be described in some detail. Patients with any primary behavioral health diagnosis over a specified time may be selected 105 and selected data acquired. Such data may be considered for purposes of this invention to have predictive value; therefore individual data categories may be referred to as predictive factors. This patient data may be obtained from claims history or historical or current patient records and will contain identifying information of the patient/member as well as certain variables such as age and gender. Thus, without limitation, pharmacy claims data, facility claims, professional services claims, enrollment/membership data, and medical records are potential sources of patient data.

Once the patients are selected 105, a patient/member table 110 may be created from the patient data of 105. The patient table 110 may then be used for merging the data with subsequent selection programs to search for selected data. Additionally, the patient data from 105 may be grouped into categories 175. For example, and without limitation, primary behavioral health diagnoses categories may comprise: adjustment disorder, anxiety, bipolar, chemical dependency, depression, eating disorder, personality disorder, psychosis, and schizophrenia.

The patient/member table 110 may be merged with at least one data source, e.g., claims data, to search for and extract predictive factor data wherein selected behavioral health diagnoses are in a secondary diagnosis position 115. For example, such data may include those patients having a secondary diagnosis of adjustment disorder, anxiety, bipolar, chemical dependency, depression, eating disorder, personality disorder, psychosis, or schizophrenia to name a few possible diagnoses.

The patient/member table 110 may also be merged with at least one data source, e.g., claims history, to collect or extract predictive factor data regarding emergency room visits for each patient in the table 120, e.g., number of emergency room visits, type of emergency room visits and time frame for the visits.

The patient/member table 110 may be also merged with at least one data sources, e.g., claims history, to collect or extract predictive factor data for claims with a primary diagnosis of behavioral health, comprising, inter alia, adjustment disorder, anxiety, bipolar, chemical dependency, depression, eating disorder, personality disorder, psychosis, or schizophrenia 125. Merge 125 may further comprise summarizing the data and assigning a label that is appropriate given the primary diagnosis.

The patient/member table 110 may also be merged with at least one data source, e.g., claims history, to search for and extract predictive factor data indicating the presence of comorbidities for, inter alia, diabetes, coronary artery disease, thyroid disease, seizures, cardiovascular disease, rheumatological diseases, infectious diseases, and gastrointestinal diseases 130. Merge 130 may further comprise assigning comorbidity categories to each patient.

The patient/member table 110 may be further merged with at least one data source, e.g., claims history, to collect or extract inpatient hospital services predictive factor data for the listed patients over a specified time period 135. Such inpatient hospital services data may be summarized into categories and time frames for each patient 140.

The patient/member table 110 may also be merged with pharmacy history and/or other data source(s) to collect or extract history of psychotropic drug use predictive factor data for the listed patients 145. Merge 145 may further comprise summarizing any drug use predictive factors into categories/drug types and time frames of use for each listed patient. A subsequent step may include summarizing any inpatient hospital services into categories and time frames for each patient 145.

The patient/member table 110 may also be merged with claims history and/or other data source(s) to collect all professional services utilized or accessed by the listed patients over a specified time period 150.

The patient/member table 110 may be merged with claims history and/or other data source(s) to collect clinical medical records data and/or patient self-reporting data relating to the presence and/or absence of predictive risk factors 152.

The ordering herein of steps 115, 120, 125, 130, 135, 140, 145, 150 and 152 are purely exemplary and to facilitate description of the inventive method. It is understood that each of the referenced method steps may be performed in any desired order and remain within the scope of the invention.

Step 155 comprises using the data obtained in merge 150 in identifying psychiatric visits for extraction of medication management predictive factor data and assigning of categories and time frames for each patient. Step 160 comprises using the data obtained in merge 150 in identifying medical office visits and assigning categories and time frames for each patient. Step 165 comprises using the data obtained in merge 150 for identifying specified services and assigning categories and time frames for each patient. Finally, step 170 comprises using the data obtained in merge 150 for identifying outpatient psychotherapy visits and assigning categories and time frames for each patient. It is understood that method steps 155, 160, 165, and 170 are not limited to the step order as described above. Therefore, the referenced steps may be performed in any order while remaining within the scope of the inventive method.

Moreover, method steps 105, 110, 115, 120, 125, 130, 35, 140, 145, 150, 155, 160, 165, 170 and 175 may be accomplished using a programmed digital computer. In this embodiment, the programmed digital computer may comprise:
a processor;
a memory operatively coupled to the processor;
a data input interface operatively coupled to the memory; and
a data output interface operatively coupled to the memory, an
   apparatus and system well understood by those skilled in the art.

The programmed digital computer may use computer code to achieve the logical functions described in each method step above. For example, the programmed digital computer may operate to pull the described list of individuals with any primary behavioral health diagnosis over a specified time period in response to at least one instruction and to store the list of the plurality of individuals in the memory. The programmed digital computer may further operate to merge the listing with at least one data source to extract behavioral health-related information in response to at least one instruction.

The next step in this embodiment of the inventive method may be entry into data analysis module 200. Thus, a master file 205 may be created using at least some of the data from the previous steps' data output, i.e., the data obtained during operation of the steps comprising the data acquisition module 100. This master file may comprise a single line per patient with all variables assigned, including categories and time frames 205. Alternatively, the master file may comprise a single line per patient, or take the form of a table of patient-specific data, comprising the predictive factor data for individual patients.

The master file patient data sets constructed in step 205 may then be run vs. the appropriate mathematical/statistical predictive model, e.g., a logistic regression model to produce probability scores for every patient represented within the master file patient data set 210. At least one of the predictive factors may be entered into the predictive model to obtain a predictive output for a particular patient. The predictive output predicts the probability that individual patients may require future hospital admission.

The logical functions described in connection with method steps 205 and 210 may be performed using a programmed digital computer as previously discussed in combination with computer code. For example, the programmed digital computer may operate to generate an output comprising the probability that the listed individuals will require a future behavioral health-related hospital admission based on at least one predictive model and in response to at least one instruction.

It is understood that at least one predictive model may be used to achieve the inventive method described herein. The at least one predictive model is designed to determine the probability of a hospital admission for each patient/member and may be applied to all patients generally. The predictive model(s) may be developed using historical and/or current patient or member data and may be further modified over time to more accurately predict the clinical outcome for individual patients. Those skilled in the art will readily recognize several possible mathematical and statistical approaches to solving this problem. For instance, ordinal, binomial or multinomial logistic regression may be employed. Ordinary least squares regression modeling may also be utilized and is within the scope of the present invention.

Further, individual predictive models may be developed and applied to cases involving specific primary diagnoses to increase the predictive success. For example, one model may be developed and applied specifically to patients with a primary diagnosis of depression. Another model may be developed and applied to those patients with a primary diagnosis of anxiety. Still another model may be developed and applied to those patients with a primary diagnosis of one type of behavioral health condition or disease wherein the identified patients also have a specific secondary diagnosis. For example, a patient with a primary diagnosis of chemical dependency and a secondary diagnosis of depression may be extremely predictive of future hospital admission and a predictive model may be developed and applied specifically for such a combination of diagnoses. Thus, it is within the scope of the invention to develop and apply predictive models to a matrix consisting of primary and secondary diagnoses and comprising the behavioral health-related conditions and diseases adjustment disorder, anxiety, bipolar, chemical dependency, depression, eating disorder, personality disorder, psychosis, or schizophrenia. The model(s) may be modified to add any of the predictive variables described herein to increase the predictive value of the output.

An exemplary predictive output is provided below for a patient (Patient 1) with a primary diagnosis of depression.

The selected Predictive Factors were analyzed within the model as either present ('1') or absent ('0') in binary fashion. Each of the Predictive Factors received appropriate weighting within the Predictive Model specific to a primary diagnosis of depression. The predictive output in this case is 0.32663.

Depressive Disorder Predictive Model Results

| Predictive Factors | Binary Results for Presence/Absence of Predictive Factors |
|---|---|
| secondary diagnosis of adjustment disorder | 1 |
| secondary diagnosis of anxiety | 1 |
| primary diagnosis of bipolar | 0 |
| secondary diagnosis of bipolar | 0 |
| primary diagnosis of chemical dependency | 0 |
| secondary diagnosis of chemical dependency | 0 |
| secondary diagnosis of depression | 1 |
| secondary diagnosis of eating disorder | 0 |
| primary diagnosis of personality disorder | 0 |
| primary diagnosis of psychosis | 0 |
| secondary diagnosis of psychosis | 0 |
| primary diagnosis of schizophrenia | 0 |
| emergency room in previous 4 months | 0 |
| emergency room for mental health in prior 7-9 months | 1 |
| inpatient admission for mental health in prior 7-9 months | 1 |
| inpatient admission for mental health in prior 4-6 months | 0 |
| inpatient admission for mental health in previous 3 months | 0 |
| non behavioral health office visits with 7 or more providers | 0 |
| 7 or more behavioral health therapy visits | 0 |
| Behavioral health therapy visits with 4 or more providers | 0 |
| prescription for a mood stabilizer drug | 1 |
| prescription for an antidepressant drug | 1 |
| drug screen in previous 3 months | 0 |
| office visit for preventive care | 1 |
| drug screen | 0 |
| ambulance service | 0 |
| Diagnosis of gastrointestinal disorders) | 0 |
| Diagnosis of coronary artery disease | 0 |
| diagnosis of cardiovascular disease | 0 |
| diagnosis of diabetes | 0 |
| Patient 1 Probability score | 0.32663 |

A second exemplary predictive output result is illustrated below for a patient (Patient 2) with a primary diagnosis of chemical dependency, wherein the predictive model is appropriately weighted using the listed Predictive Factors. As may be seen, the predictive output in this case is 0.885021.

Chemical Dependency Predictive Model Results

| Predictive Factors | Binary Results for Presence/Absence of Predictive Factors |
|---|---|
| secondary diagnosis of attention deficit disorder | 0 |
| secondary diagnosis of anxiety | 0 |
| primary diagnosis of bipolar | 0 |
| secondary diagnosis of bipolar | 0 |
| secondary diagnosis of chemical dependency | 1 |
| primary diagnosis of depression | 1 |
| secondary diagnosis of depression | 1 |
| primary diagnosis of eating disorder | 0 |
| primary diagnosis of psychosis | 0 |
| secondary diagnosis of schizophrenia | 1 |
| inpatient admission for chemical dependency | 1 |
| inpatient admission for non behavioral health in previous 3 months | 1 |
| inpatient admission for chemical dependency in prior 10-12 months | 1 |
| inpatient admission for chemical dependency in prior 7-9 months | 0 |
| inpatient admission for chemical dependency in previous 3 months | 0 |
| 10 or more office visits for non behavioral health | 0 |
| 7 or more behavioral health therapy visits | 1 |
| prescription for an antidepressant drug | 0 |
| prescription for analgesic narcotics | 0 |
| office visit for preventive care | 0 |
| hospital outpatient for drug or alcohol rehab | 0 |
| hospital outpatient for psychiatric services | 0 |
| diagnosis for infectious diseases | 0 |
| diagnosis of CVD | 0 |
| diagnosis of diabetes | 1 |
| diagnosis of seizure | 0 |
| Patient 2 probability score | 0.885021 |

When the probability scores are obtained for each patient, the inventive method may enter the identification module 300. Here, the probability data obtained in 210 are further analyzed to create a listing or file of the top probability scores for patients with a given variable label 305. For example, the listing may comprise the top 1% of probability scores for patients with the depression label and/or the top 5% and/or at least the top 10% of probability scores for a particular predictive factor, or combination of predictive factors, e.g., primary diagnosis and/or secondary diagnosis for behavioral health. It is understood that there is much flexibility in step 305 in that the top probability score threshold or cutoff may be modified, e.g., from 1% to 3%, and any variable label contained in the probability scoring step 210 may be used for ranking patients.

The logical functions described in connection with method step 305 may be performed using a programmed digital computer as previously discussed in combination with computer code. For example, the programmed digital computer may operate to identify the high-risk individuals from the predictive model output in response to at least one instruction.

The interventional management module 400 is a proactive component of the inventive method whereby identified high-risk patients and/or members are engaged by caseworkers that assist in reducing the identified risk. Such intervention may comprise providing support for compliance with the healthcare provider's treatment plan, addressing psychosocial needs (including barriers to complying with treatment plans), coordinating care among providers and/or providing individualized problem solving support. The intervention may occur either telephonically or in person or a combination thereof. An individualized action plan for each engaged member is developed and involves the combined efforts of the identified patient member, the healthcare provider(s), and the assigned caseworker, at a minimum. This action plan reduces the likelihood of hospitalization by improving the clinical symptoms and associated risk factor(s).

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for predicting and minimizing future behavioral health-related hospital admissions, comprising:
   compiling a listing consisting of all individuals with any primary behavioral health disease and/or condition diagnosis over a specified time period;
   merging the listing with at least one data source, wherein the at least one data source comprises claims history, billing records, pharmaceutical history, historical patient records, and/or patient self-reporting data, to extract at least one behavioral health-related predictive factor;
   assigning a weighting to the at least one behavioral health-related predictive factor to create a weighted at least one behavioral health-related predictive factor;
   determining if the at least one behavioral health-related predictive factor is present or absent for each individual in the compiled listing, wherein the presence or absence of the at least one behavioral health-related predictive factor is assigned a "1" or a "0", respectively, in binary fashion;
   generating, based on at least one predictive model that analyzes the weighted at least one behavioral health-related predictive factor, including the determined presence or absence of the at least one behavioral health-related predictive factor, a predictive output comprising the quantitative probability that the individuals listed with any primary behavioral health diagnosis will require a future behavioral health-related hospital admission, thereby predicting which of the individuals listed with any primary behavioral health disease and/or condition diagnosis will require a future behavioral health-related hospital admission;
   identifying the individuals listed with any primary behavioral health diagnosis will require a future behavioral health-related hospital admission from the predictive model output; and
   referring the individuals identified as listed with any primary behavioral health diagnosis that will require a future behavioral health-related hospital admission to caseworkers for intervening with the individuals identified as listed with any primary behavioral health diagnosis and who are predicted to require a future behavioral health-related hospital admission to reduce, eliminate or mitigate risk factors to reduce the risk of the identified individuals being admitted to a hospital in the future; and
   providing a programmed digital computer, the programmed digital computer comprising a processor; a memory operatively coupled to the processor; a data input interface operatively coupled to the memory; computer code stored in the memory; and a data output interface operatively coupled to the memory, the computer code capable of accomplishing the logical functions of compiling, merging, generating, identifying, referring and intervening.

2. The method of claim 1, wherein the compiling further comprises obtaining behavioral health-related data for individuals from historical data sources.

3. The method of claim 2, further comprising obtaining the data from current data sources.

4. The method of claim 1, wherein the merging further comprises acquiring data indicating a secondary diagnosis of behavioral health conditions.

5. The method of claim 1, wherein the merging further comprises acquiring data indicating emergency room visits.

6. The method of claim 1, wherein the merging further comprises acquiring data indicating comorbidities for behavioral health-related hospital admissions.

7. The method of claim 1, wherein the merging further comprises acquiring data indicating inpatient hospital service utilization.

8. The method of claim 1, wherein the merging further comprises acquiring data indicating utilization of all professional services.

9. The method of claim 1, wherein the merging further comprises acquiring data regarding history of psychotropic drug use.

10. The method of claim 1, wherein at the least one predictive factor is inserted into the at least one predictive model to generate the predictive output.

11. The method of claim 1, wherein the at least one predictive model is specific to individual primary diagnoses.

12. The method of claim 1, wherein the at least one predictive model is specific to individual secondary diagnoses.

13. The method of claim 1, wherein the at least one predictive model is specific to individual primary and individual secondary diagnoses.

14. The method of claim 1, wherein the identifying further comprises selecting the patients in a selected percentage of the predictive output.

15. The method of claim 1, wherein the identifying further comprises selecting the patients in the upper 5% of the predictive output.

16. The method of claim 1, wherein the identifying further comprises selecting the patients in the upper 1% of the predictive output.

17. The method of claim 1, further comprising using a computer program product comprising computer code which is executed by the programmable computer for the compiling, merging, identifying and generating.

18. A computer program product for predicting and minimizing future behavioral health-related hospital admissions, the computer program product stored and executable on a programmed digital computer comprising a processor; a memory operatively coupled to the processor; a data input interface operatively coupled to the memory; computer code stored in the memory; and a data output interface operatively coupled to the memory, comprising:
   computer code for compiling a listing including all individuals with any primary behavioral health disease and/or condition diagnosis over a specified time period;
   computer code for merging the listing with at least one data source, wherein the at least one data source comprises claims history, billing records, pharmaceutical history, historical patient records, and/or patient self-reporting data, to extract at least one behavioral health-related predictive factor;
   computer code for assigning a weighting to the at least one behavioral health-related predictive factor;
   computer code for determining if the at least one behavioral health-related predictive factor is present or absent for each individual in the compiled listing, wherein the presence or absence of the at least one behavioral health-related predictive factor is assigned a "1" or a "0", respectively, in binary fashion;
   computer code for generating, based on at least one predictive model that analyzes the weighted at least one behavioral health-related predictive factor, including the determined presence or absence of the at least one behavioral
health-related predictive factor, a predictive output comprising the quantitative probability that the individuals listed will require a future behavioral health-related hospital admission, thereby predicting which of the individuals will require a future behavioral health-related hospital admission;
computer code for identifying the individuals with any primary behavioral health diagnosis over a specified time period and also predicted to require a future behavioral health-related hospital admission from the predictive model output; and
referring the generated output of the individuals with any primary behavioral health diagnosis over a specified time period and also predicted to require a future behavioral health-related hospital admission to caseworkers for intervening with the identified individuals, wherein the computer code is executed on the programmable computer.

19. A system for predicting and minimizing future behavioral health-related hospital admissions, comprising:
a programmed digital computer, the programmed digital computer further comprising:
a processor;
a memory operatively coupled to the processor;
a data input interface operatively coupled to the memory; and
a data output interface operatively coupled to the memory;
computer code stored in the memory which, when executed by
the programmed digital computer, operates to pull a list of individuals with any primary behavioral health disease and/or condition diagnosis over a specified time period in response to at least one instruction and to store the list of the plurality of individuals in the memory;
computer code stored in the memory which, when executed by
the programmed digital computer, operates to merge the listing with at least one data source, wherein the at least one data source comprises claims history, billing records, pharmaceutical history, historical patient records, and/or patient self-reporting data, to extract behavioral health-related information in response to at least one instruction;
computer code stored in the memory which, when executed by the programmed digital computer, operates to assign a weighting to the at least one behavioral health-related predictive factor in response to at least one instruction;
computer code stored in the memory which, when executed by the programmed digital computer, operates to determine if the at least one behavioral health-related predictive factor is present or absent for each individual in the compiled listing, wherein the presence or absence of the at least one behavioral health-related predictive factor is assigned a "1" or a "0", respectively, in binary fashion in response to at least one instruction;
computer code stored in the memory which, when executed by the programmed digital computer, operates to generate an output comprising the quantitative probability that the listed individuals will require a future behavioral health-related hospital admission based on at least one predictive model that analyzes the weighted at least one behavioral health-related predictive factor, including the determined presence or absence of the at least one behavioral health-related predictive factor, and in response to at least one instruction;
computer code stored in the memory which, when executed by the programmed digital computer, operates to identify the individuals with any primary behavioral health diagnosis over a specified time period and also predicted to require a future behavioral health-related hospital admission from the quantitative predictive model output in response to at least one instruction, and wherein the individuals with any primary behavioral health diagnosis over a specified time period and also predicted to require a future behavioral health-related hospital admission are referred to caseworkers for intervening.

* * * * *